United States Patent [19]

Espino et al.

[11] Patent Number: 5,290,781
[45] Date of Patent: Mar. 1, 1994

[54] KETANESERINOL AS AN AGENT TO REDUCE INTRAOCULAR PRESSURE

[75] Inventors: Ramon L. Espino, Riverside; Donald G. Musson, Upland; Orest Olejnik, Trabuco Canyon, all of Calif.

[73] Assignee: Iolab Corporation, Claremont, Calif.

[21] Appl. No.: 954

[22] Filed: Jan. 5, 1993

[51] Int. Cl.$^5$ ............................................. A61K 31/505
[52] U.S. Cl. ...................................... 514/259; 514/913
[58] Field of Search ................ 514/259, 913; 544/285

[56] References Cited

PUBLICATIONS

Biosis Abstract of Eur J Clin Pharmacol 32(3). 1987. 259-266. Persson et al.

Primary Examiner—Zohreh A. Fay
Attorney, Agent, or Firm—Joseph J. Brindisi

[57] ABSTRACT

This invention relates to the use of ketanserinol as an ophthalmic therapeutic agent to reduce intraocular pressure and its method of use for treating glaucoma by systemic administration of ketanserinol, it salts, esters or prodrugs to a patient or more particularly, topically administering ketanserinol and salts thereof to the eye of a patient.

6 Claims, 4 Drawing Sheets

FIG-1

KETANESERINOL AS AN AGENT TO REDUCE INTRAOCULAR PRESSURE

FIELD OF THE INVENTION

This invention relates to ophthalmic therapeutic agents to reduce intraocular pressure and methods of treating glaucoma. More particularly, this invention relates to the use of ketanserinol, its salts, esters and prodrugs, as ophthalmic therapeutic agents to reduce intraocular pressure and their method of use as well as methods of treating glaucoma by administering ketanserinol topically to the eye of a patient or by administering ketanserinol systemically.

BACKGROUND OF THE INVENTION

Glaucoma is an ocular disorder most often characterized by increased intraocular pressure which, over time, may cause impaired vision or blindness. Treatment may involve topical agents such as pilocarpine (a cholinomimetic drug); timolol (a Beta-adrenergic blocking agent); epinephrine (an alpha and beta adrenergic receptor antagonist); dipevefrin (a prodrug of epinephrine) and demecarium bromide (a cholinesterase inhibitor). Systemic agents used to treat glaucoma include carbonic anhydrase inhibitors such as acetazolamide.

Ketanserin, a systemic anti-hypertensive agent, is an antagonist of the actions of serotonin (5-HT) that has been characterized as highly specific for $S_2$ (5-$HT_2$) receptors. Ketanserinol is the main metabolite of ketanserin. Ketanserin is disclosed in U.S. Pat. No. 4,335,127 as an anticongestive. The ketanserinol metabolite is obtained by enzymatic reduction of ketanserin in biological systems according to the following reaction:

KETANSERIN  →  KETANSERIN-OL

W. Meuldermans, J. Hendrick, W. Lauwers, E. Swysen, R. Hurkmans, F. Knaeps, R. Woestenborghs, J. Heykants, "Excretion and Biotransformation of Ketanserin after Oral and Intravenous Administration in Rats and Dogs", Drug Metab. Dispos., (1984) 12:772-781 and W. Meuldermans, et al., Arch. Int. Pharmacodyn, (1985) 274:330, disclose methods for carrying out this reaction. The entire disclosure of both of these references are hereby incorporated herein by reference.

Systemically, ketanserin is enzymatically reduced to ketanserinol and excreted in the urine and feces and is approximately 1000 times less active as an anti-hypertensive agent than ketanserin. Ketanserin is also reduced to ketanserinol in the eye.

Intraocular Pressure (IOP) effects have been previously investigated for ketanserin see, F. W. Change et al. "Mechanism of the Ocular Hypotensive Action of Ketanserin," J. Ocular Pharmacol., 1(2):137-147 (1985); C. Costagliola et al., "Effect of Oral Ketanserin Administration on Intraocular Pressure in Glaucomatous Patients", Exp. Eye Res. (1991), 52, 507-510; and M. Cellini, A. Baldi, R. Caramazza "Ketanserin and Intraocular Pressure: A Preliminary Study", New Trends in Ophthalmology, Vol. VI, No. 2/1991 127-130 (1991), however, ketanserinol intraocular pressure effects have not been studied.

It is an object of the present invention to provide an agent for reducing the effects of intraocular pressure on the eye and to provide a treatment for glaucoma. It has been found by the present inventors that the ocular activity of ketanserinol on IOP is far superior to that of ketanserin and is comparable to commercially existing anti-glaucoma products.

It is a further object of the present invention to use ketanserinol as an effective agent for treatment of glaucoma by lowering intraocular pressure.

SUMMARY OF THE INVENTION

As embodied and broadly described herein the present invention provides an ophthalmic therapeutic agent or composition to reduce intraocular pressure comprising an effective intraocular pressure (IOP) reducing amount of ketanserinol. Ketanserinol may be provided in a racemic mixture form, or in the substantially pure R isomer or S isomer thereof or esters, salts and prodrugs thereof.

In preferred embodiments of the invention ketanserinol is provided in an ophthalmic therapeutic topical solution formulation comprising in weight by weight of the total composition:

| | |
|---|---|
| ketanserinol | 0.01-5.0% |
| a non-ionic surfactant | 0.00-2.0%; |
| a tonicity agent | 0.25-6.0%; |
| a preservative | 0.001-1.0%; |
| a stabilizing agent | 0.001-1.0%; |
| a chelating agent | 0.001-0.5%; and |
| a buffering system to control pH in the range of | 4.0-8.0 |

In preferred embodiments the non-ionic surfactant comprises one or a mixture of two or more compounds selected from the group consisting of sorbitan fatty acid esters and lecithin.

The tonicity agent is selected from the group consisting of: sodium chloride, potassium chloride, dextrose, mannitol and mixtures thereof.

In preferred embodiments the buffering system comprises agents useful in preparing buffers selected from the group consisting of: acetic acid, boric acid, hydrochloric acid, phosphoric acid, potassium carbonate, potassium citrate, potassium phosphates, sodium acetate, sodium bicarbonate, sodium biphosphate, sodium borate, sodium carbonate, sodium citrate, sodium hydroxide, sodium phosphate, sulfuric acid and mixtures thereof.

In preferred embodiments the preservative is selected from the group consisting of: benzalkonium chloride, benzethonium chloride, chlorobutanol, phenylmercuric acetate, phenylmercuric nitrate, thimerosal, methylparaben, propylparaben, sodium benzoate, sorbic acid and mixtures thereof.

In preferred embodiments the stabilizing agent is selected from the group consisting of: disodium edetate (metal-chelating agent), citric acid (reducing agent), sodium metabisulfite (reducing agent), ascorbic acid (reducing agent), acetyl cysteine (reducing agent) and mixtures thereof.

A suspension of ketanserinol may be prepared by the addition from about 0.01 to 10.0% of a suspending agent to the topical formulation provided above. In preferred embodiments the suspending agent is selected from the group consisting of: carbomer, carboxymethylcellulose calcium, carboxymethylcellulose sodium, cellulose, microcrystalline cellulose, hydroxyethylcellulose, hydroxypropylcellulose, hydroxypropylmethylcellulose, methylcellulose, polyethylene oxide, polyvinyl alcohol, povidone, dextrin, propylene glycol and mixtures thereof.

As embodied and described herein the invention is also directed to methods of reducing intraocular eye pressure in a patient comprising the step of topically administering an intraocular pressure reducing effective amount of ketanserinol to the eye of a patient.

In preferred embodiments ketanserinol is provided in an ophthalmic therapeutic topical formulation to lower intraocular pressure as described above.

In other embodiments of the invention a method of treating glaucoma by reducing intraocular eye pressure in a patient is provided comprising the step of topically administering a pressure reducing and therapeutically effective amount of ketanserinol to the eye of a patient.

In other embodiments intraocular eye pressure is reduced in a patient by systemically introducing a pressure reducing effective amount of ketanserinol to a patient. In preferred embodiments the systemic introduction is carried out by oral administration.

DETAILED DESCRIPTION OF THE PREFERRED EMBODIMENTS

To achieve the objects of the invention, reference will now be made in detail to preferred embodiments of the invention. Examples of which are illustrated in the following examples section.

As embodied and broadly described herein the invention comprises an ophthalmic therapeutic agent to lower intraocular pressure comprising an effective intraocular pressure reducing amount of ketanserinol. Ketanserinol is an asymmetric compound and is normally available as a racemic mixture of the R and S isomer. The present invention may provide ketanserinol in either the racemic mixture form or in a substantially pure R isomer or S isomer. Preferably, the ketanserinol will be provided in the form which is the most active and therefore, most effective for reducing intraocular pressure. Ketanserinol salts, esters and prodrugs thereof such as for example ketanserinol acetate, may also be utilized in accordance with the invention. Such esters or prodrugs may provide desirable characteristics such as sustained release or sustained activity.

Effective amounts of ketanserinol for reducing intraocular pressure is believed to be in the broad range of about 0.25 to 1.0 mg/dose for topical treatment of the human eye. Optimal concentration and an effective amount of ketanserinol for treating intraocular eye pressure can be determined by routine experimentation by those skilled in the art. Preferably, the concentration of ketanserinol in topical formulations is in the range of 0.01 to 5.0% and more preferably, about 0.50 to 1.0% of ketanserinol as a racemic mixture. The concentrations for the substantially pure R or S isomer thereof would be about 0.25 to 0.5% weight by weight of the total formulation.

In preferred embodiments of the invention the ketanserinol is provided in an ophthalmic therapeutic formulation which can be topically applied to an eye to lower intraocular pressure. A preferred solution formulation comprises:

| | |
|---|---|
| ketanserinol | 0.01–5.0%; |
| a non-ionic surfactant | 0.01–2.0%; |
| a tonicity agent | 0.25–6.0%; |
| a preservative | 0.001–1.0%; |
| a stabilizing agent | 0.001–0.5%; |
| a chelating agent | 0.001–0.5%; and |
| a buffering system to control pH in the range of | 4.0–8.0. |

The ketanserinol in the formulation may be in racemic mixture form, or in the form of the substantially pure R isomer or S isomer thereof.

The non-ionic surfactant comprises one or a mixture of two or more compounds selected from the group consisting of sorbitan fatty acid esters, lecithin, and mixtures thereof. The tonicity agent is selected from the group consisting of: sodium chloride, potassium chloride, dextrose, mannitol and mixtures thereof. The buffering system comprises agents useful in preparing buffers selected from the group consisting of: acetic acid, boric acid, hydrochloric acid, phosphoric acid, potassium carbonate, potassium citrate, potassium phosphates, sodium acetate, sodium bicarbonate, sodium biphosphate, sodium borate, sodium carbonate, sodium citrate, sodium hydroxide, sodium phosphate, sulfuric acid and mixtures thereof. The preservative is selected from the group consisting of: benzalkonium chloride, benzethonium chloride, chlorobutanol, phenylmercuric acetate, phenylmercuric nitrate, thimerosal, methylparaben, propylparaben, sodium benzoate, sorbic acid and mixtures thereof. The stabilizing agent is selected from the group consisting of: disodium edetate (metal-chelating agent), citric acid (reducing agent), sodium metabisulfite (reducing agent), ascorbic acid (reducing agent), acetyl cysteine (reducing agent) and mixtures thereof.

For suspension formulations, from about 0.01 to 10.0% of a suspending agent is added which may be selected from the group consisting of: carbomer, carboxymethylcellulose calcium, carboxymethylcellulose sodium, cellulose, microcrystalline cellulose, dextrin, hydroxyethylcellulose, hydroxypropylcellulose, hydroxypropylmethylcellulose, methylcellulose, polyethylene oxide, polyvinyl alcohol, povidone, propylene glycol and mixtures thereof.

As embodied and broadly described herein the invention is also directed to a method of reducing intraocular eye pressure comprising the step of introducing an effective amount of ketanserinol to the eye of a patient. In other embodiments the ketanserinol may be topically administered to the eye of a patient or orally administered. A method of treating a mammalian or human patient suffering from the symptoms of glaucoma by reducing the intraocular eye pressure in a patient is also a part of the present invention. Lowering of intraocular pressure, e.g. in the treatment of glaucoma is carried out by administering the ketanserinol solution or suspension as an eyedrop to a patient. The dosage used will depend on the severity of the patient's condition but will generally be in an effective dosage range of about 0.25 to 1.0 mg/dose. A method of treatment may include topically applying one to two drops of a ketanserinol solution or the suspension to the eye of a patient on a regimen of between two to four times per day.

EXAMPLES

The invention will now be illustrated by examples. The examples are not intended to be limiting of the scope of the present invention but read in conjunction with the detailed and general description above, provide further understanding of the present invention and an outline of a process for preparing the compositions of the invention and methods of practicing the invention.

The ketanserinol used in Examples I-III is obtained by the method disclosed in U.S. Pat. No. 4,335,127, specifically at Column 36, lines 15-27 (Example XXXVIII), the entire disclosure of this reference is hereby incorporated herein by reference.

In particular, 0.545 g of ketanserin free base is mixed in 250 ml of methanol in a 500 ml round bottom flask. 0.6 g of NaBH$_4$ is added to the methanolic solution/suspension and mixed at room temperature. The white mixture turns clear within 5 minutes. The solution may then be stirred overnight. 2 ml of water is added to the solution and it is rotary evaporated to dryness in the round bottom flask. The residue is mixed with 50 ml of water and stirred. A major portion of the solid residue dissolves into the water. The solution is warmed to complete dissolution and filtered. The filtrate is placed in a refrigerator overnight.

A first crop of ketanserinol crystallizes from the solution and the crystals are filtered and the filtrate is returned to the refrigerator for a second crop (next day). The total yield obtained is 0.472 g (86.2%). The material was characterized by HPLC, IR and melting point, i.e., 216.1° C. The compound can be recrystallized from methanol. The other compounds and compositions used in the Examples are those which are commercially available.

EXAMPLE I

Ketanserinol Solution

| | |
|---|---|
| ketanserinol | 1.0% (w/v) |
| benzalkonium chloride, USP (BAK) | 0.01% (w/v) |
| disodium edetate, USP | 0.01% (w/v) |
| sodium chloride, USP (NaCl) | 0.9% (w/v) |
| sodium hydroxide or hydrochloric acid | pH 5.6 |
| distilled water q.s. | 100% |

A. The vehicle is prepared in a 100 ml volumetric flask.
 1. Into the above flash weigh 0.90 g of NaCl, USP.
 2. 10 mg of solid BAK or the equivalent weight from a diluted BAK solution.
 3. 10 mg of disodium edetate.
 4. Fill to volume with distilled deionized water and stir or sonicate to dissolve the components of 1-3.

B. Weigh 100 mg of ketanserinol into a 10 ml volumetric flask.
 1. Add about 6-7 ml of vehicle (A).
 2. Lower the pH to about 2.5 with 1N HCl and sonicate or stir to dissolve completely (ketanserinol is stable at low pH).
 3. Add vehicle (from A) to about 9.0 ml volume.
 4. Adjust pH between 5.5-6.0 with 1N NaOH.
 5. Fill to volume with vehicle A.
 6. Stir to homogenize the solution, the final pH should be 6 and the osmolarity between 270-330 mOsm.
 7. Filter through a suitable 0.22μ filter and analyze by HPLC for final concentration. The concentration should be between 98% and 102%.

EXAMPLE II

Ketanserinol Solution

| | |
|---|---|
| ketanserinol | 1.0% (w/v) |
| polysorbate 80, USP | 0.05% (w/v) |
| disodium edetate | 0.01 (w/v) |
| benzalkonium chloride NF | 0.01% (w/v) |
| citric acid | 0.71% (w/v) |
| disodium hydrogen phosphate | 1.87% (w/v) |
| sodium chloride USP | 0.30% (w/v) |
| sodium hydroxide or hydrochloric acid | pH 6.0 |
| distilled water q.s. | 100% |

A. The vehicle is prepared in a 100 ml volumetric flask.
 1. Into the above flask weigh 50 mg of polysorbate 80, USP grade.
 2. Weigh 10 mg of disodium edetate USP or NF grade.
 3. Weigh 10 mg of benzalkonium chloride solid or the equivalent from a BAK Solution; USP or NF grade.
 4. Weigh 0.71 g of Citric Acid, USP.
 5. Weigh 1.87 g of disodium hydrogen phosphate, USP or NF grade.
 6. Weigh 0.300 g of sodium chloride, USP grade.
 7. Add 50 ml of distilled deionized water.
 8. Stir to dissolve completely.

B. Ketanserinol prepared in a 50 ml volumetric flash.
 1. Into a 50 ml volumetric flask weigh 1 g of ketanserinol.
 2. Add 40 ml of distilled deionized water.
 3. Lower the pH with concentrated HCl between 2.0 and 2.5 and dissolve by sonicating or stirring.

C. Mixing of Solution A and B.
 1. Slowly add Solution B into Solution A with constant stirring.
 2. Rinse flask B with about 5 ml of distilled water into flask A.
 3. Slowly adjust the pH to 6 with 10% sodium hydroxide.
 4. Measure the osmolarity (270-330 mOsm).
 5. Filter through a suitable 0.22μ filter, and analyze by HPLC.

EXAMPLE III

1.0% Ketanserinol Suspension

|  | % | gr/2 l. |
|---|---|---|
| ketanserinol | 1.0% | 20 |
| hydroxypropyl methylcellulose (90 HG 4000 cps USP) | 0.6% | 12 |
| sodium phosphate dibasic, USP | 0.6% | 12 |
| sodium citrate (dihydrate), USP | 0.3% | 6 |
| edetate disodium, USP | 0.1 | 2 |
| polysorbate 80, NF | 0.05% | 1 |
| sodium chloride, USP | 0.46% | 9.2 |
| benzalkonium chloride, NF | 0.01% | 0.2 |
| 10% sodium hydroxide or 10% hydrochloric acid to | pH 7.2 | |
| purified water, q.s. to | 100% | |

A. The vehicle is prepared in a 2 liter, stainless steel or glass container, add approximately 1.4 liter of purified water and heat to 80° C.–90° C. with stir bar. Add and dissolve with constant agitation 12.0 g of hydroxypropyl methylcellulose. Cool the solution to approximately 40° C. Add and dissolve, with constant agitation: sodium citrate 5.0 g, sodium phosphate dibasic 1.0 g, polysorbate 80 1.0 g, sodium chloride 9.2 g, edetate disodium 2.0 g. Check pH. Adjust to approximately pH 7.2 with 10% hydrochloric or 10% sodium hydroxide. Add and dissolve, with constant agitation the required amount of ketanserinol. Heat the solution to 60° C., if necessary, to aid dissolution. Filter the solution aseptically through a 0.22μ cartridge filter of equivalent membrane into a sterile holding vessel, previously calibrated to 2 liters.

B. In a 1 liter stainless steel or glass container, add approximately 500 ml of purified water with a stirring bar. Add and dissolve, with constant agitation: sodium citrate 1.0 g, sodium phosphate dibasic 11.0 g. Check pH. Adjust if necessary to approximately pH 9.0 with 10% sodium hydroxide solution. Slowly filter solution B aseptically through a 0.22μ cartridge filter or equivalent filtering membrane into the holding vessel containing solution. A stir vehicle in holding vessel constantly. Aseptically check pH. Aseptically adjust pH to range 6.8–7.4, if necessary, sterile 10% sodium chloride or sterile 10% hydrochloric acid. Aseptically bring suspension volume to 2 liter with sterile purified water. Mix thoroughly. Aseptically fill the product into sterile bottles. Stir the suspension constantly through the filling procedure.

EXAMPLE IV

Preparation of R- and S- Enantiomers of Ketanserinol Racemate

Ketanserinol (0.25 g) is dissolved in methanol (10 ml), heated to reflux. D(−)-tartaric acid or L(+)-tartaric acid (0.1 g), is added to the hot solution. The methanol is heated until both the alcohol and tartaric acid are dissolved; the solution is then filtered through a coarse Whatman filter. The filtration is cooled (0°–5° C.) to facilitate crystallization of the tartrate salt.

Identification and purity is determined by circular dichroism and HPLC-UV, respectively.

The substantially pure R- or S- enantiomer of ketanserinol is then prepared in a solution or suspension in accordance with any one of Examples I–III above.

EXAMPLE V

Preparation of Ketanserinol Esters

Ketanserinol tartrate of Example IV was converted to its hydrochloride salt as follows: Ketanserinol tartrate was dissolved in warm water (9100 ml). Sodium hydroxide (1M) was added to give a pH 10 and the mixture was extracted with ether (2×75 ml). The extracts were dried over anhydrous sodium sulphate and a slight excess of 3M HCl in methanol was added. Petroleum ether was added and after standing overnight at 4° C. the white crystalline precipitate formed was filtered off and recrystallized from acetone-ether to give ketanserinol hydrochloride.

Ketanserinol hydrochloride was slurried in 12 ml of benzene. The appropriate acyl chloride was added and the slurry was refluxed for two hours. After cooling, the mixture was evaporated in vacuo. Benzene (10 ml) was added and the mixture was evaporated again to remove traces of the acyl chloride. The solid residue was slurred in ether, filtered off and washed and washed again in ether. Recrystallization of the ketanserinol esters is performed using a mixture of alcohol-ether solvents. Structures are confirmed by NMR and IR. Preparation of ketanserinol acetate may be carried out in accordance with Example XXXIX of U.S. Pat. No. 4,335,127 at Column 36, lines 28–43.

Comparison Studies of Ketanserinol for Reducing Intraocular Pressure Versus Ketanserin and Commercial Products.

Ketanserin was obtained from Janssen Pharmaceutica, N.V. the assignee of U.S. Pat. No. 4,335,127 which discloses ketanserin and its method of preparation. Ketanserin (1%) was formulated in an isotonic mannitol (5.09%) solution at pH 4.0. Ketanserinol (1.0%) was formulated in a normal saline solution at pH 5.2.

The commercial products, 2% PILOCAR ® (IOLAB Corporation) and 0.5% TIMOPTIC ® (0.5% timolol, and a phosphate buffer) (Merck Sharp & Dohme), were used as received.

For normotensive intraocular pressure (IOP) studies, a group of eight (8) NZW male rabbits weighing 1.9–2.5 kg. were used. The rabbits were initially dosed with normal saline in both eyes to obtain IOP baseline. Every three days the rabbits were dosed with the drug by applying 1 drop (25 μl) into the conjunctival sac of the animal's right eye (via a pipettor). Similarly, the contralateral eye was treated with one drop of normal saline. Intraocular Pressure (IOP) measurements were obtained using a Digilab Modular One ™ Pneuma Tonometer from Bio-Rad Corporation.

IOP baseline was obtained every 30 minutes for 90 minutes (−90–0). At time zero, one drop of drug was applied to the animal eye. After treatment, IOP readings were obtained every 30 minutes up to 300 minutes.

For water-loaded Intraocular Studies (IOP), a group of six (6) NZW female rabbits weighing 1.5–2.5 kg. were used. The animals were dosed with the drug in the same manner as the normotensive rabbits. IOP baseline was obtained for 90 minutes prior to water-loading, the drug was applied to the right eye and normal saline to the left eye. Water loading (t=0) was used to induce hypertension. A gastric tube was inserted over the tongue, down the esophagus and into the stomach. 60 ml/Kg of distilled water was administered via the gastric tube. IOP measurements were obtained at 0.5, 1.0, 2.0, 3.0, 4.0, 5.0, and 6.0 hours after water-loading. Protocols for IOP Studies were found in Appendix I.

RESULTS AND DISCUSSION

Results of these comparison studies are provided in Tables 1-3 below and illustrated in the graphs of FIGS. 1-4.

In a normotensive study of NZW rabbits, the IOP activity of 1.0% concentration solutions of ketanserinol to ketanserin were compared. Also, ketanserinol was compared to two commercial products, 0.5% timolol and 2.0% pilocar. In hypertensive rabbits, the hypotensive activity of ketanserinol was investigated in water-loaded rabbits. 1.0% Ketanserinol solution was compared to 2.0% pilocar solution. The dose response curve of 0.5%, 1.0%, and 1.5% ketanserinol, using normal saline and timolol was compared as the negative and positive controls.

Figure 1:
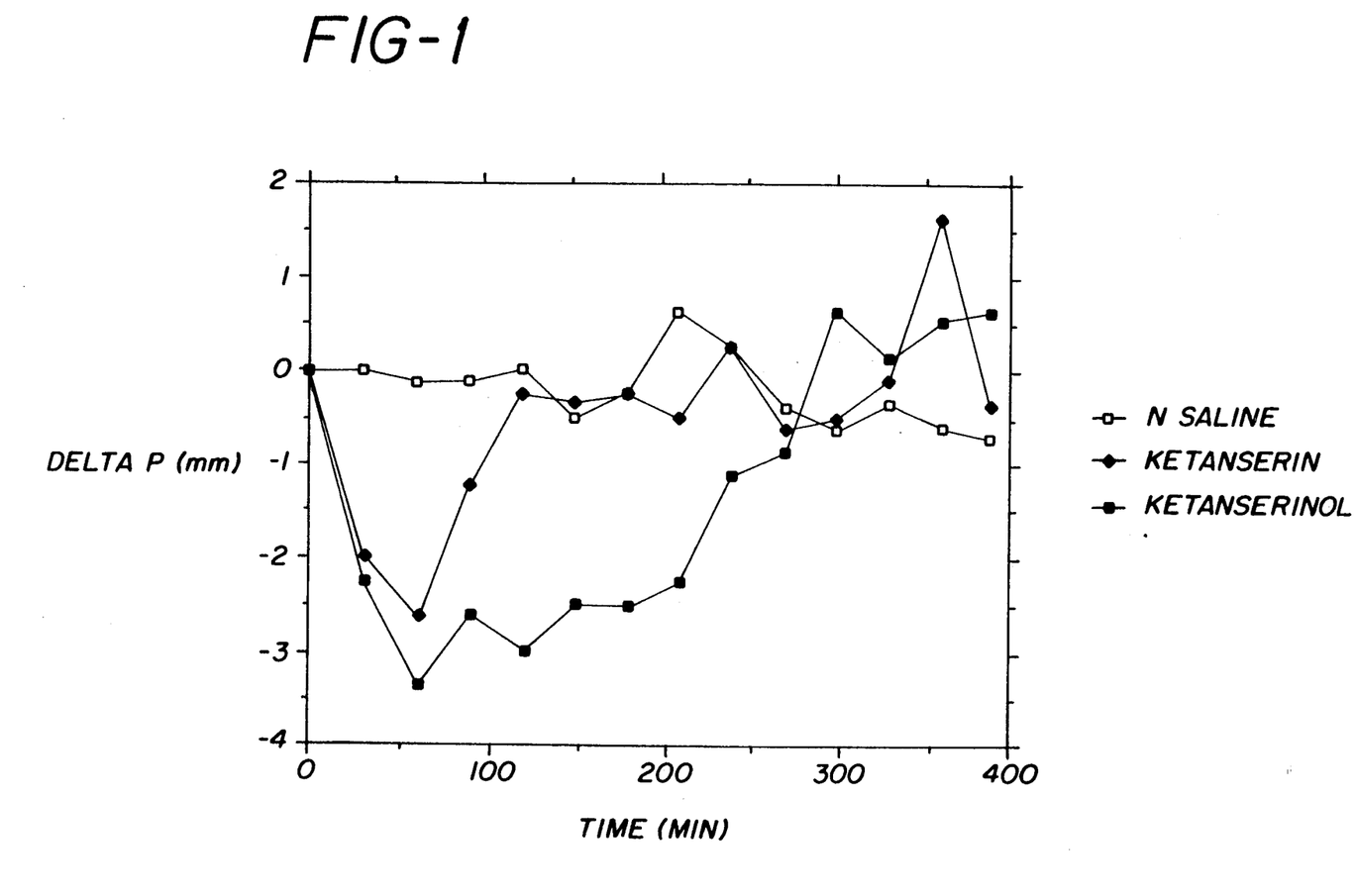
FIG. 1 is a graphic depiction of the results of an IOP study of ketanserin versus ketanserinol.
Figure 2:
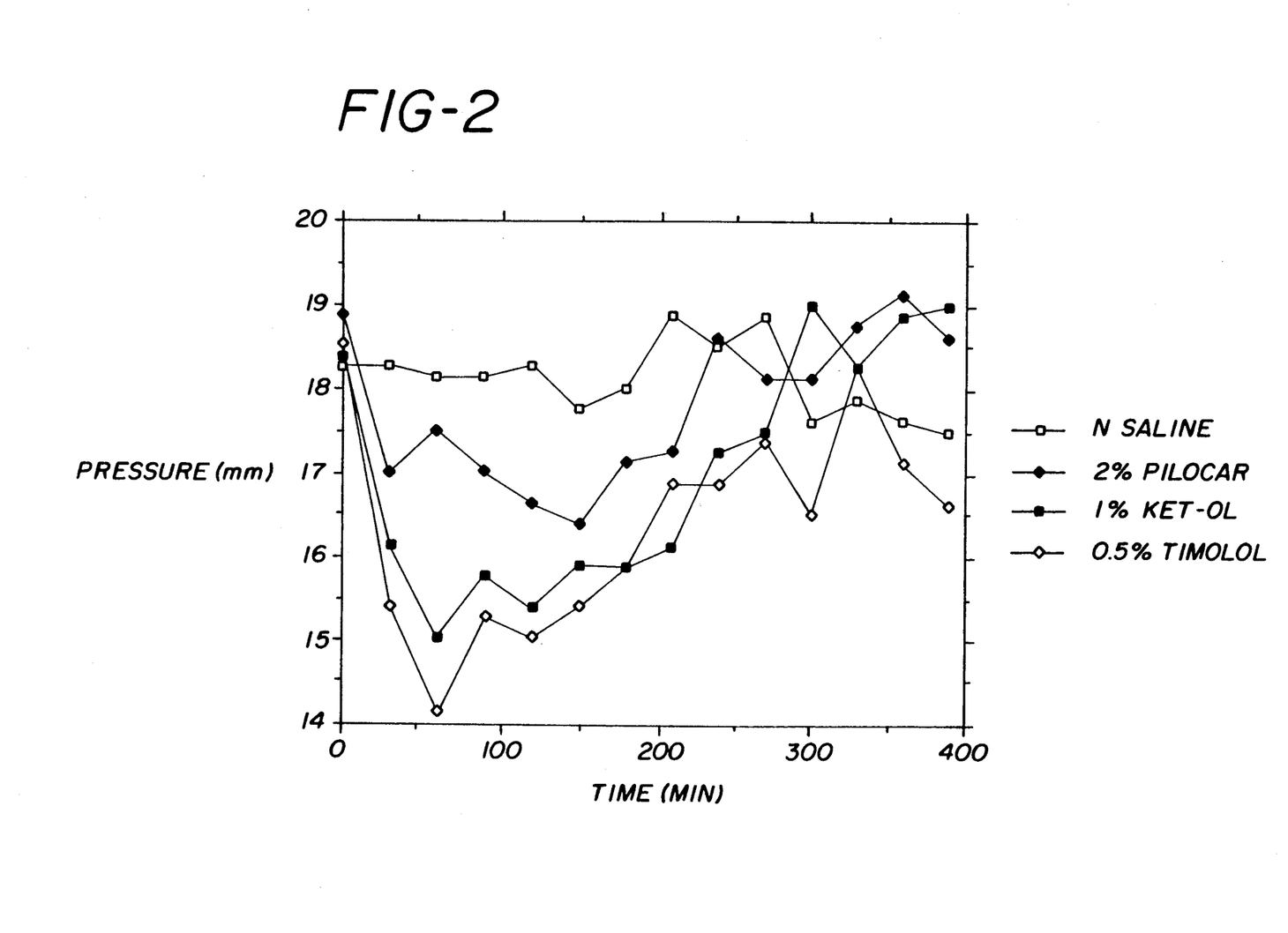
FIG. 2 is a graphic depiction of the results of an IOP study of 1% ketanserinol versus pilocar, saline and timolol in normotensive rabbits.

The results obtained for normotensive and hypertensive rabbits are found in Tables 1, 2, and 3 respectively. The results, in normotensive rabbits, clearly indicate that ketanserinol lowers IOP better than ketanserin, and has 2 times its lasting effect (FIG. 1); the results further show that 1.0% ketanserinol is as effective as 2.0% pilocar but not as effective as 0.5% timolol (FIG. 2). It is noted that the IOP profile of ketanserinol, within experimental error, follows the IOP pattern of timolol up to 270 minutes.

Figure 3:
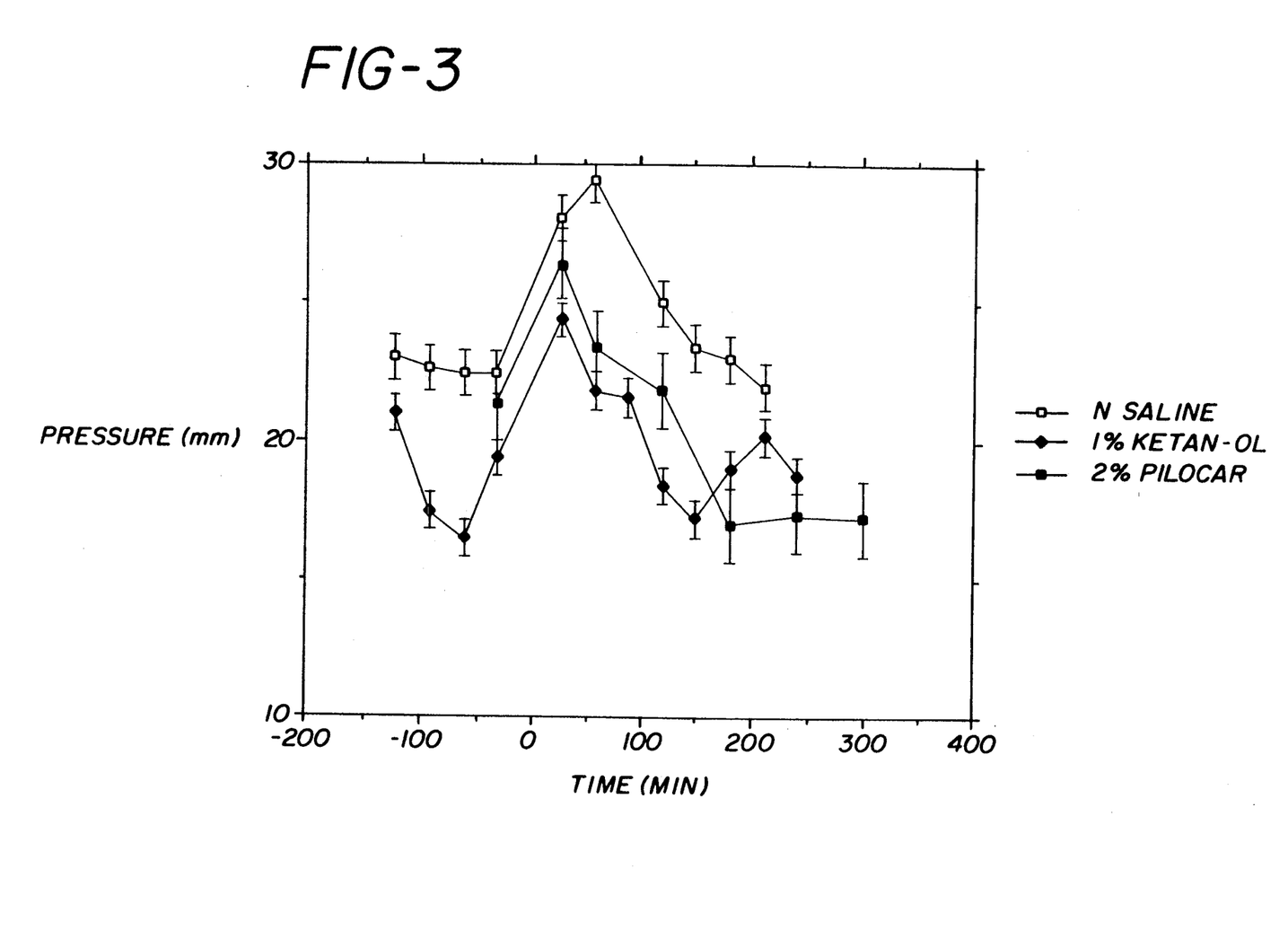
FIG. 3 is a graphic depiction of the results of an IOP study of 2% pilocar versus 1% ketanserinol in water loaded NZW rabbits.
Figure 4:
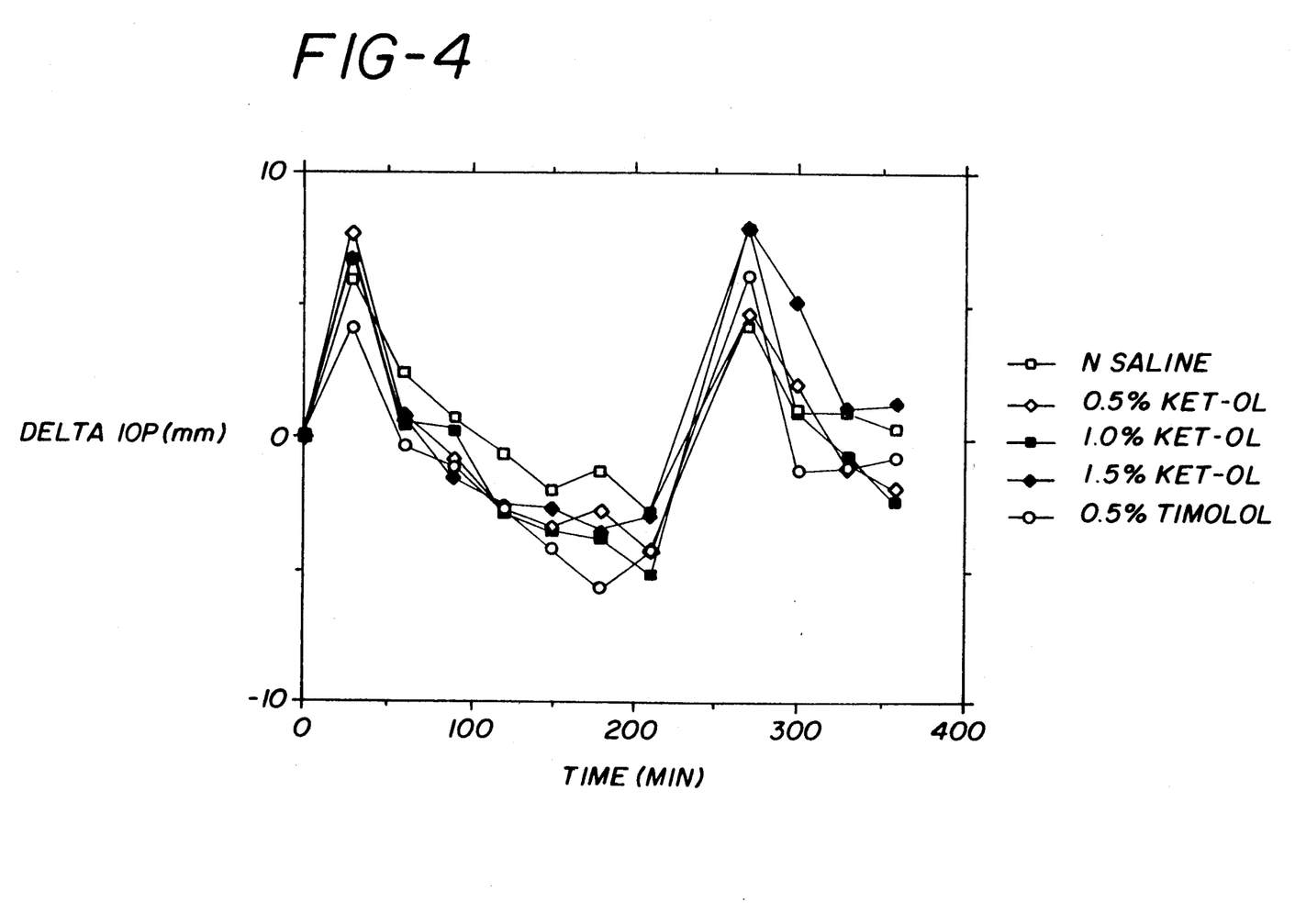
FIG. 4 is a graphic depiction of the results of an IOP study of dose response of ketanserinol.

The water-loaded study, shows that ketanserinol lowers IOP in hypertensive rabbits; the results are found in Table 2. 1.0% Ketanserinol lowers the IOP as well as 2.0% pilocar in water-loaded NZW rabbits (FIG. 3). In the dose response studies, the IOP activity of 1.0% ketanserinol is equivalent to the IOP activity of 0.5% timolol (See FIG. 4).

TABLE 2-continued

Intraocular Pressure studies (IOP) of 1.0% Ketanserinol, 2.0% pilocar and 0.9% Nacl (control) in Water-loaded NZW rabbits (n = 6).

| Time (min) | N Saline | SD | 1% Ketan-ol | SD | 2% Pilocar | SD |
|---|---|---|---|---|---|---|
| 210.000 | 22.000 | 2.450 | 20.200 | 2.950 | | |
| 240.000 | | | 18.800 | 3.110 | 17.330 | 3.500 |
| 300.000 | | | | | 17.160 | 0.750 |

TABLE 3

Intraocular Pressure (IOP) Dose Response Curve for 0.5%, 1.0%, and 1.5% Ketanserinol in Water-loaded Rabbits (N = 10)

| | Time (min) | N Saline | 0.5% Ket-ol | 1.0% Ket-ol | 1.5% Ket-ol | 0.5% Timolol |
|---|---|---|---|---|---|---|
| 1 | 0.000 | 0.000 | 0.000 | 0.000 | 0.000 | 0.000 |
| 2 | 30.000 | 6.130 | 7.750 | 4.200 | 6.790 | 6.930 |
| 3 | 60.000 | 2.420 | 0.880 | −0.360 | 0.790 | 0.510 |
| 4 | 90.000 | 0.700 | −0.750 | −1.110 | −1.580 | 0.300 |
| 5 | 120.000 | −0.580 | −2.750 | −2.740 | −2.580 | −2.950 |
| 6 | 150.000 | −2.010 | −3.370 | −4.240 | −2.710 | −3.570 |
| 7 | 180.000 | −1.150 | −2.750 | −5.740 | −3.460 | −3.820 |
| 8 | 210.000 | −2.870 | −4.370 | −4.360 | −2.960 | −5.200 |
| 9 | 240.000 | | | | | |
| 10 | 270.000 | 4.420 | 4.750 | 6.140 | 7.920 | 7.930 |
| 11 | 300.000 | 0.990 | 2.000 | −1.280 | 5.170 | 1.050 |
| 12 | 330.000 | 0.990 | −1.010 | −1.110 | 1.170 | −0.700 |
| 13 | 360.000 | 0.420 | −1.970 | −0.740 | 1.290 | −2.420 |

The scope of the present invention is not limited by the description, examples and suggested uses herein, and modifications can be made without departing from the spirit of the invention. For example, the ketanserinol can be provided in a sustained release solution or suspension for topical or oral application. Preparation of pharmaceutical compositions and medical application of methods of the present invention can be accom-

TABLE 1

Data for Intraocular Pressure studies in NZW normotensive rabbits, Right Eye, (n = 8).

| | Time (min) | N Saline | SD | 1% Ketanserin | SD | 1% Ketanserinol | SD | 2% Pilocar | SD | 0.5% Timolol | SD |
|---|---|---|---|---|---|---|---|---|---|---|---|
| 1 | 0.000 | 18.250 | 1.830 | 16.250 | 0.880 | 18.375 | 2.060 | 18.875 | 0.991 | 18.500 | 1.770 |
| 2 | 30.000 | 18.250 | 1.830 | 14.250 | 1.670 | 16.125 | 1.880 | 17.000 | 1.300 | 15.375 | 1.300 |
| 3 | 60.000 | 18.125 | 1.880 | 13.620 | 1.140 | 15.000 | 1.410 | 17.500 | 2.140 | 14.125 | 1.450 |
| 4 | 90.000 | 18.125 | 1.960 | 15.125 | 2.030 | 15.750 | 2.540 | 17.000 | 1.930 | 15.250 | 2.370 |
| 5 | 120.000 | 18.250 | 1.660 | 16.000 | 1.850 | 15.370 | 1.760 | 16.625 | 2.970 | 15.000 | 1.770 |
| 6 | 150.000 | 17.750 | 2.050 | 15.875 | 1.450 | 15.875 | 1.246 | 16.375 | 1.770 | 15.375 | 2.065 |
| 7 | 180.000 | 18.000 | 2.270 | 16.000 | 1.690 | 15.875 | 1.550 | 17.125 | 2.690 | 15.875 | 1.640 |
| 8 | 210.000 | 18.875 | 1.450 | 15.750 | 1.900 | 16.125 | 2.350 | 17.250 | 1.280 | 16.875 | 1.960 |
| 9 | 240.000 | 18.500 | 2.563 | 16.500 | 1.850 | 17.250 | 2.430 | 18.625 | 2.390 | 16.875 | 1.810 |
| 10 | 270.000 | 17.875 | 2.167 | 15.630 | 1.300 | 17.500 | 2.226 | 18.125 | 1.810 | 17.375 | 2.130 |
| 11 | 300.000 | 17.625 | 1.598 | 15.750 | 1.160 | 19.000 | 2.670 | 18.125 | 2.530 | 16.500 | 1.690 |
| 12 | 330.000 | 17.875 | 1.356 | 16.140 | 1.570 | 18.250 | 2.310 | 18.750 | 1.670 | 18.250 | 1.580 |
| 13 | 360.000 | 17.625 | 2.326 | 17.850 | 2.730 | 18.875 | 1.880 | 19.125 | 2.750 | 17.125 | 2.030 |
| 14 | 390.000 | 17.500 | 2.390 | 17.378 | 1.340 | 19.000 | 2.620 | 18.625 | 1.770 | 16.625 | 1.500 |

TABLE 2

Intraocular Pressure studies (IOP) of 1.0% Ketanserinol, 2.0% pilocar and 0.9% Nacl (control) in Water-loaded NZW rabbits (n = 6).

| Time (min) | N Saline | SD | 1% Ketan-ol | SD | 2% Pilocar | SD |
|---|---|---|---|---|---|---|
| −120.000 | 23.000 | 2.340 | 21.000 | 5.050 | | |
| −90.000 | 22.600 | 2.300 | 17.400 | 4.390 | | |
| −60.000 | 22.400 | 1.820 | 16.400 | 2.190 | | |
| −30.000 | 22.400 | 3.360 | 19.400 | 4.500 | 21.330 | 3.260 |
| 0.000 | | | | | | |
| 30.000 | 28.000 | 5.240 | 24.400 | 5.120 | 26.330 | 2.660 |
| 60.000 | 29.400 | 6.840 | 21.800 | 3.110 | 23.330 | 3.260 |
| 90.000 | | | 21.600 | 2.960 | | |
| 120.000 | 25.000 | 5.780 | 18.400 | 3.130 | 21.830 | 2.480 |
| 150.000 | 23.400 | 1.510 | 17.200 | 1.090 | | |
| 180.000 | 23.000 | 2.450 | 19.000 | 1.580 | 17.000 | 3.100 | plished by any manufacturing, clinical, medical, and pharmaceutical method and technique as would be presently or prospectively known to those skilled in the art. Thus, it is intended that the present invention cover the modifications and variations of this invention provided that they come within the scope of the appended claims and their equivalents.

What is claimed is:

1. A method of reducing intraocular eye pressure in a patient comprising the step of topically administering a pressure reducing effective amount of ketanserinol to the eye of a patient.

2. The method of claim 1 wherein the ketanserinol is in racemic mixture form, or is the substantially pure R isomer or S isomer thereof.

3. A method of reducing intraocular eye pressure in a patient comprising the step of topically administering a pressure reducing effective amount of ketanserinol and salats thereof to the eye of a patient.

4. A method of reducing intraocular eye pressure in a patient comprising the step of topically administering a pressure reducing effective amount of a ketanserinol ester or prodrug to the eye of a patient.

5. A method of treating glaucoma by reducing intraocular eye pressure in a patient comprising the step of orally or parenterally administering a pressure reducing effective amount of ketanserinol and salts thereof to a patient.

6. A method of treating glaucoma by reducing intraocular eye pressure in a patient comprising the step of orally or parenterally administering a pressure reducing effective amount of a ketanserinol ester or prodrug to a patient.

* * * * *